United States Patent [19]

Böger et al.

[11] 4,140,795
[45] Feb. 20, 1979

[54] PESTICIDAL 1,3,5-TRIAZAPENTA-1,4-DIENES

[75] Inventors: Manfred Böger, Weil am Rhine, Fed. Rep. of Germany; Odd Kristiansen, Möhlin, Switzerland; Ernst Beriger, Allschwil, Switzerland; Jozef Drabek, Oberwil, Switzerland; Dieter Dürr, Bottmingen, Switzerland; Kurt Rüfenacht, Basel, Switzerland

[73] Assignee: Ciba-Geigy Corporation, Ardsley, N.Y.

[21] Appl. No.: 856,369

[22] Filed: Dec. 1, 1977

[30] Foreign Application Priority Data

Dec. 9, 1976 [CH] Switzerland .............. 15497/76
Feb. 2, 1977 [CH] Switzerland .............. 1244/77
Nov. 8, 1977 [CH] Switzerland .............. 13586/77

[51] Int. Cl.$^2$ .................. C07C 143/75; A01N 9/16
[52] U.S. Cl. .................. 424/304; 260/465 E; 260/556 A; 260/556 F; 424/321
[58] Field of Search .......... 260/465 E, 556 A, 556 F; 424/304, 321; 260/564 R

[56] References Cited

U.S. PATENT DOCUMENTS

| 3,818,070 | 6/1974 | Wollweber et al. ........ 260/556 A X |
| 3,912,779 | 10/1975 | Tarnow et al. ............... 424/321 X |
| 4,011,343 | 3/1977 | Leeming et al. ............. 424/326 |
| 4,017,638 | 4/1977 | Dittrich et al. ............ 260/556 A X |
| 4,056,570 | 11/1977 | Pallos ........................ 260/556 A X |

FOREIGN PATENT DOCUMENTS 949285 9/1956 Fed. Rep. of Germany ...... 260/556 A
2405546 8/1975 Fed. Rep. of Germany ...... 260/564 R Primary Examiner—Thomas Waltz
Attorney, Agent, or Firm—Frederick H. Rabin

[57] ABSTRACT 1,3,5-Triazapenta-1,4-dienes of the formula

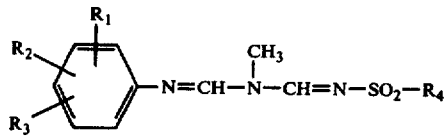

wherein each of $R_1$, $R_2$ and $R_3$ represents hydrogen, halogen, $C_1$-$C_4$alkyl, $C_1$-$C_4$alkoxy, trifluoromethyl or cyano, and $R_4$ represents $C_1$-$C_4$alkyl which is unsubstituted or substituted by halogen, a process for their manufacture and their use in pest control.

10 Claims, No Drawings

PESTICIDAL 1,3,5-TRIAZAPENTA-1,4-DIENES

The present invention relates to 1,3,5-triazapenta-1,4-dienes, to a process for their manufacture and to their use in pest control.

The 1,3,5-triazapenta-1,4-dienes have the formula

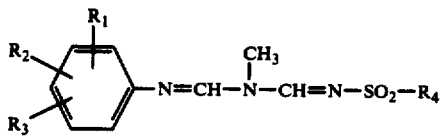
(I)

wherein each of $R_1$, $R_2$ and $R_3$ represents hydrogen, halogen, $C_1$–$C_4$ alkyl, $C_1$–$C_4$ alkoxy, trifluoromethyl or cyano, and $R_4$ represents $C_1$–$C_4$ alkyl which is unsubstituted or substituted by halogen.

By halogen is meant fluorine, chlorine, bromine or iodine, in particular chlorine or bromine. The alkyl or alkoxy groups represented by $R_1$ to $R_4$ can be straight-chain or branched. Examples of such groups include: methyl, methoxy, ethyl, ethoxy, propyl, propoxy, n-butyl, n-butoxy, isobutyl, sec-butyl, tert-butyl.

Preferred compounds on account of their action are those of the formula I in which each of $R_1$, $R_2$ and $R_3$ represents hydrogen, chlorine, bromine, methyl, trifluoromethyl, methoxy or cyano, and $R_4$ represents methyl or chloromethyl.

The compounds of the formula I can be obtained by methods which are known per se, for example by reacting a compound of the formula

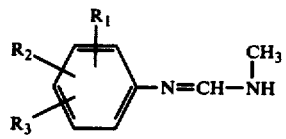

wherein $R_1$, $R_2$ and $R_3$ are as defined in formula I, with a compound of the formula

RO—CH=N—SO$_2$R$_4$ in which $R_4$ is as defined in formula I and R represents $C_1$–$C_4$ alkyl.

The process is carried out at a temperature between 0° and 120° C., preferably between 40° and 100° C., under normal or elevated pressure and optionally in a solvent or diluent. Examples of suitable solvents or diluents are: ethers and ethereal compounds, such as diethyl ether, dipropyl ether, dioxane, dimethoxyethane and tetrahydrofurane; amides, such as N,N-dialkylated carboxamides; aliphatic, aromatic and halogenated hydrocarbons, in particular benzene, toluene, xylene, chloroform and chlorobenzene; nitriles, such as acetonitrile; dimethyl sulphoxide; ketones, such as acetone and methyl ethyl ketone.

The starting materials of the formulae II and III are known or they can be prepared by methods analogous to known ones.

The compounds of the formula I are suitable for controlling a variety of animal and plant pests. In particular, they have an outstanding action against insects and representatives of the order Acarina. They are therefore suitable for example for controlling mites and ticks of the species Tetranychus and Panonychus and of the families Dermanyssidae and Ixodidae as well as for controlling insects for example of the families: Tettigoniidae, Gryllidae, Gryllotalpidae, Blattidae, Reduviidae, Pyrrhocoridae, Cimicidae, Delphacidae, Aphididae, Diaspididae, Pseudococcidae, Scarabaeidae, Dermestidae, Coccinellidae, Tenebrionidae, Chrysomelidae, Bruchidae, Tineidae, Noctuidae, Lymantriidae, Pyralidae, Culicidae, Tipulidae, Stomoxydae, Trypetidae, Muscidae, Calliphoridae and Pulicidae.

In particular, the compounds of the formula I are suitable for controlling insects which are harmful to plants, especially insects which damage plants by eating, in ornamentals and crops of useful plants, especially in cotton plantations (e.g. Spodoptera littoralis and Heliothis virescens) and in vegetable crops (for example Leptinotarsa decemlineata and Myzus persicae).

The active compounds of the formula I also have a very good action against flies, for example Musca domestica and mosquito larvae.

The insecticidal and/or acaricidal action can be substantially broadened and adapted to prevailing circumstances by addition of other insecticides and/or acaricides. Examples of suitable additives include: organic phosphorous compounds, nitrophenols and derivatives thereof, formamidines, ureas, pyethroids, carbamates, and chlorinated hydrocarbons.

Compounds of the formula I are also combined with particular advantage with substances which exert a potentiating effect. Examples of such compounds include: piperonyl butoxide, propynyl ether, propynyl oximes, propynyl carbamates and propynyl phosphonates, 2-(3,4-methylenedioxyphenoxy)-3,6,9-trioxaundecane, S,S,S-tributylphosphorotrithioate.

The compounds of the formula I may be used as pure active substance or together with suitable carriers and/or additives. Suitable carriers and additives can be solid or liquid and correspond to the substances conventionally used in the art of formulation, for example natural or regenerated substances, solvents, dispersants, wetting agents, tackifiers, thickeners, binders and/or fertilisers.

For application, the compounds of the formula I may be processed to dusts, emulsifiable concentrates, granules, dispersions, sprays, to solutions, or suspensions, in the conventional formulation which is commonly employed in application technology. In addition, cattle dips and spray races, in which aqueous preparations are used, may also be mentioned.

The compositions of the present invention are prepared in known manner by homogeneously mixing and/or grinding active substances of the formula I with the suitable carriers, with or without the addition of dispersants or solvents which are inert to the active substances.

The compounds of the formula I may be processed to the following formulations:
Solid formulations:
Dusts, tracking powders and granules (coated granules, impregnated granules and homogeneous granules).
Liquid formulations:
(a) water-dispersible active substance concentrates: wettable powders, pastes and emulsions;
(b) solutions.

The content of active substance in the above described compositions is between 0.1% and 95%.

The compounds (active substances) of the formula I can, for example, be formulated as follows (throughout the present specification all parts and percentages are by weight):

DUSTS

The following substances are used to manufacture (a) a 5% and (b) a 2% dust:
(a) 5 parts of active substance, 95 parts of talc;
(b) 2 parts of active substance, 1 part of highly disperse silicic acid, 97 parts of talc.

The active substances are mixed with the carriers and ground.

GRANULES

The following substances are used to produce 5% granules:
5 parts of active substance,
0.25 parts of epichlorohydrin,
0.25 parts of cetyl polyglycol ether,
3.50 parts of polyethylene glycol,
91 parts of kaolin (particle size 0.3 - 0.8 mm).

The active substance is mixed with epichlorohydrin and the mixture is dissolved in 6 parts of acetone; the polyethylene glycol and cetyl polyglycol ether are then added. The resultant solution is sprayed on kaolin, and the acetone is subsequently evaporated in vacuo.

WETTABLE POWDERS:

The following constituents are used for the preparation of (a) a 40%, (b) and (c) a 25%, and (d) a 10% wettable powder:
(a) 40 parts of active substance,
5 parts of sodium ligninsulphonate,
1 part of sodium dibutylnaphthalenesulphonate,
54 parts of silicic acid.
(b) 25 parts of active substance,
4.5 parts of calcium ligninsulphonate,
1.9 parts of Champagne chalk/hydroxyethyl cellulose mixture (1:1),
1.5 parts of sodium dibutylnaphthalenesulphonate,
19.5 parts of silicic acid,
19.5 parts of Champagne chalk,
28.1 parts of kaolin,
(c) 25 parts of active substance,
2.5 parts of isooctylphenoxy-polyoxyethyleneethanol,
1.7 parts of Champagne chalk/hydroxyethyl cellulose mixture (1:1),
8.3 parts of sodium aluminium silicate,
16.5 parts of dieselguhr,
46 parts of kaolin;
(d) 10 parts of active substance,
3 parts of a mixture of the sodium salts of saturated fatty alcohol sulphates,
5 parts of naphthalenesulphonic acid/formaldehyde condensate,
82 parts of kaolin.

The active substances are homogeneously mixed with the additives in suitable mixers and the mixture is then ground in appropriate mills and rollers. Wettable powders are obtained which can be diluted with water to give suspensions of the desired concentration.

EMULSIFIABLE CONCENTRATES:

The following substances are used to produce (a) a 10%, (b) a 25%, and (c) a 50% emulsifiable concentrate:
(a) 10 parts of active substance,
3.4 parts of epoxidised vegetable oil,
3.4 parts of a combination emulsifier consisting of fatty alcohol polyglycol ether and alkylarylsulphonate calcium salt,
40 parts of dimethyl formamide,
43.2 parts of xylene;
(b) 25 parts of active substance,
2.5 parts of epoxidised vegetable oil,
10 parts of alkylarylsulphonate/fatty alcohol polyglycol ether mixture,
5 parts of dimethyl formamide,
57.5 parts of xylene;
(c) 50 parts of active substance,
4.2 parts of tributylphenol-polyglycol ether,
5.8 parts of calcium dodecylbenzenesulphonate,
20 parts of cyclohexanene,
20 partx of xylene.

By diluting these concentrates with water it is possible to obtain emulsions of the required concentration.

SPRAYS:

The following ingredients are used to prepare (a) a 5% spray, and (b) a 95% spray:
(a) 5 parts of active substance,
1 part of epichlorohydrin,
94 parts of ligroin (boiling range 160°-190° C.);
(b) 95 parts of active substance,
5 parts of epichlorohydrin.

The invention is further illustrated by the following Examples.

EXAMPLE 1

Preparation of N-(2-methyl-4-chlorophenyl)-N'-methyl-N''-methylsulphonyl-1,3,5-triazapenta-1,4-diene To a solution of 18.2 g of N-(2-methyl-4-chlorophenyl)-N'-methylformamidine in 60 ml of abs. dioxane are added dropwise at room temperature 15.1 g of N-ethoxymethylenemethanesulphonamide and the solution is stirred for 1 hour at 60° C. The reaction mixture is subsequently concentrated and the crystallised product is recrystallised from toluene, affording the compound of the formula

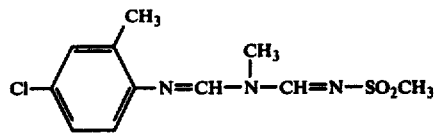

as a white powder with a melting point of 142°-143° C. The following compounds are also prepared in analogous manner:

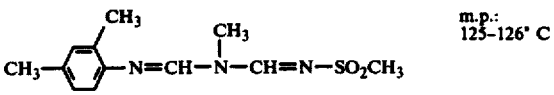

m.p.: 125-126° C

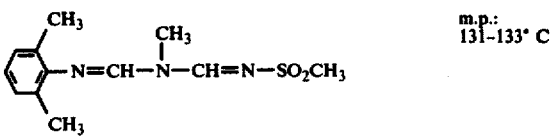

m.p.: 131-133° C

-continued

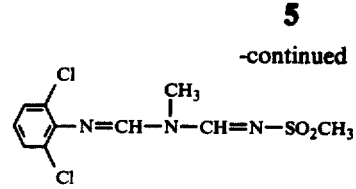
m.p.: 163–164° C

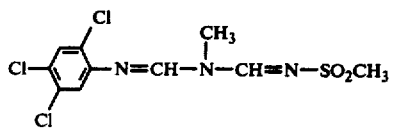
m.p.: 189–190° C

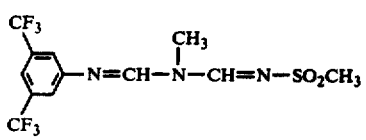
m.p.: 157–158° C

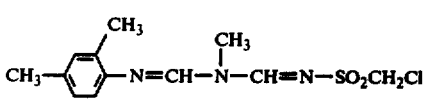
m.p.: 127–128° C

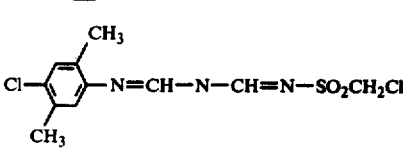
m.p.: 167–169° C

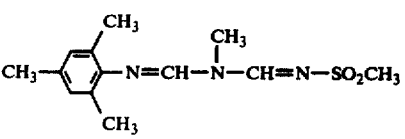
m.p.: 144–146° C

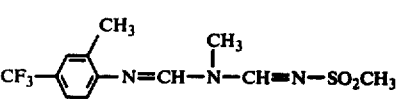
m.p.: 154–155° C

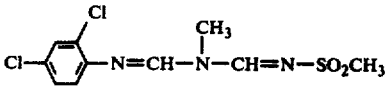
m.p.: 154–155° C

EXAMPLE 2

(A) Insecticidal stomach poison action

Cotton plants were sprayed with a 0.05% aqueous emulsion of active substance (obtained from a 10% emulsifiable concentrate). After the spray coating had dried, the cotton plants were populated with Spodoptera littoralis and Heliothis virescens in the $L_3$-stage. The test was carried out at 24° C. and 60% relative humidity.

In this test, the compounds of Example 1 exhibited a good insecticidal stomach poison action against Spodoptera and Heliothis larvae.

(B) Systemic insecticidal action

To determine the systemic action, bean plants (Vicia fabia) which had grown roots were put into a 0.01% aqueous solution of active substance (obtained from a 10% emulsifiable concentrate). Twenty four hours later, the parts of the plants above the soil were populated with aphids (Aphis fabae). By means of a special device the aphids were protected from any possible contact with the test substance either directly or via the gas phase. The test was carried out at 24° C. and 70% relative humidity.

In this test, the compounds of Example 1 exhibited a systemic insecticidal action against Aphis fabae.

EXAMPLE 3

Action against Chilo suppressalis

Rice seedlings of the variety Caloro were transplanted into plastic pots (6 plants per pot) having a diameter of 17 cm at the top and reared to a height of about 60 cm. Infestation with Chilo suppressalis larve ($L_1$-stage, 3 to 4 mm in length) took place two days after the addition of active substance in granule form (rate of application: 8 kg of active ingredient per hectare) to the paddy water. Evaluation of the insecticidal action was made 10 days after addition of the granules.

In this test, the compounds of Example 1 acted against Chilo suppressalis.

EXAMPLE 4

Acaricidal action

Twelve hours before the test for acaricidal action, Phaseolus vulgaris plants were populated with an infested piece of leaf from a mass culture of Tetranychus urticae. The mobile stages which had migrated to the plants were sprayed with the emulsified test preparations from a chromatography atomiser in such a way that the spray broth did not run off. The number of living and dead larvae, adults and eggs was evaluated under a stereoscopic microscope after 2 to 7 days and the result expressed in percentage values. During the test run, the plants stood in greenhouse compartments at 25° C.

In this test, the compounds of Example 1 acted against adults, larvae and eggs of Tetranychus urticae.

EXAMPLE 5

Action against soil nematodes

To test the action against soil nematodes, the active substances were homogeneously mixed with soil infected with root gall nematodes (meloidgyne arenaria). Young tomato plants were planted in the treated soil in one test run immediately afterwards and then 8 days later further tomatoes were sown in a second test run.

The nematicidal action was evaluated by counting the number of galls present on the roots 28 days after planting and sowing respectively. In this test, the active compounds of Example 1 exhibited a good action against meloidogyne arenaria.

EXAMPLE 6

Action on ticks (A) Rhipicephalus bursa

Five adult ticks and 50 tick larvae were counted into each of a number of test tubes and immersed for 1 to 2 minutes in 2 ml of an aqueous emulsion containing a concentration of 100, 10, 1 or 0.1 ppm of test substance. Each test tube was then sealed with a cotton-wool plug and placed on its head to enable the cotton wool to absorb the active substance emulsion.

The adults were evaluated after 2 weeks and the larvae after 2 days. Each test was repeated twice.

(B) BOOPHILUS MICROPLUS (LARVAE)

Tests were carried out with 20 OP-sensitive and 20 OP-resistant larvae using aqueous emulsions similar to those used in Test A. (The resistance refers to the tolerance towards diazinone). The compounds of Example 1 acted in these tests against adults and larvae of Rhipicephalus bursa and OP-sensitive and OP-resistant larvae of Boophilus microplus.

What is claimed is:

1. A 1,3,5-triazapenta-1,4-diene of the formula

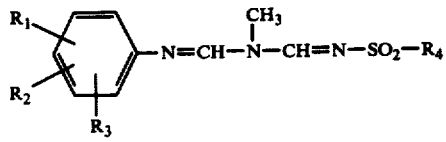

wherein each of $R_1$, $R_2$ and $R_3$ represents hydrogen, halogen, $C_1$–$C_4$alkyl, $C_1$–$C_4$alkoxy, trifluoromethyl or cyano, and $R_4$ represents $C_1$–$C_4$alkyl which is unsubstituted or substituted by halogen.

2. A 1,3,5-triazapenta-1,4-diene according to claim 1 wherein each of $R_1$, $R_2$ and $R_3$ represents hydrogen, chlorine, bromine, methyl, trifluoromethyl, methoxy or cyano, and $R_4$ represents methyl and chloromethyl.

3. The 1,3,5-triazapenta-1,4-diene according to claim 2 of the formula

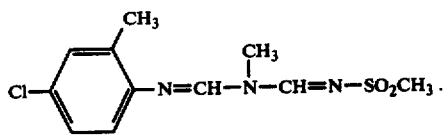

4. The 1,3,5-triazapenta-1,4-diene according to claim 2 of the formula

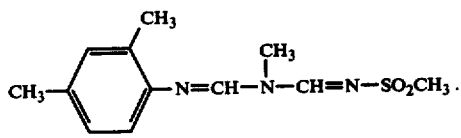

5. The 1,3,5-triazapenta-1,4-diene according to claim 2 of the formula

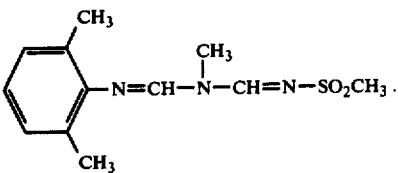

6. The 1,3,5-triazapenta-1,4-diene according to claim 2 of the formula

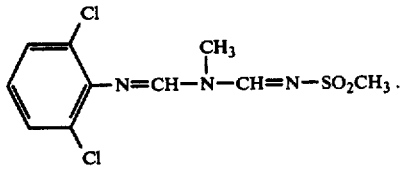

7. The 1,3,5-triazapenta-1,4-diene according to claim 2 of the formula

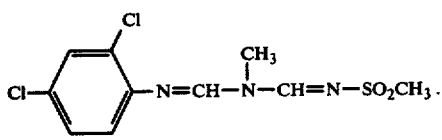

8. The 1,3,5-triazapenta1,4-diene according to claim 2 of the formula

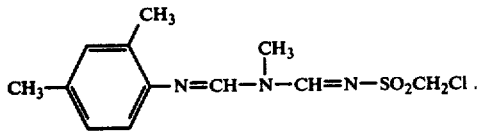

9. A insecticidal and acaricidal composition which contains as active component an effective insecticidal and acaricidal amount of a 1,3,5-triazapenta-1,4-diene according to claim 1, and suitable carriers, additives or mixtures thereof.

10. A method of controlling insects and acarids which comprises the application thereto of an effective insecticidal and acaricidal amount of a 1,3,5-triazapenta-1,4-diene according to claim 1.

* * * * *